United States Patent [19]
Fayolle et al.

[11] Patent Number: 6,040,154
[45] Date of Patent: Mar. 21, 2000

[54] PROCESS FOR BACTERIAL TREATMENT OF EFFLUENTS THAT CONTAIN ETHYL-TERT-BUTYL ETHER

[75] Inventors: Francoise Fayolle, Clamart; Francoise Le Roux, Rueil Malmaison; Jean-Paul Vandecasteele, Fiyrqyeyxm, all of France

[73] Assignee: Institut Francais du Petrole, Rueil-Malmaison Cedex, France

[21] Appl. No.: 09/120,841

[22] Filed: Jul. 23, 1998

[30] Foreign Application Priority Data

Jul. 23, 1997 [FR] France .................................. 97 09455

[51] Int. Cl.$^7$ ................ C12P 39/00; B09B 3/00

[52] U.S. Cl. ................ 435/42; 435/262; 435/262.5; 435/830; 435/832; 435/863

[58] Field of Search .................. 435/42, 262, 262.5, 435/830, 832, 863

[56] References Cited

U.S. PATENT DOCUMENTS

| | | | |
|---|---|---|---|
| 5,750,364 | 5/1998 | Salanitro | 435/42 |
| 5,811,010 | 9/1998 | Salanitro | 210/610 |
| 5,814,514 | 9/1998 | Steffan et al. | 435/262 |

*Primary Examiner*—Herbert J. Lilling
*Attorney, Agent, or Firm*—Millen, White, Zelano & Branigan, P.C.

[57] ABSTRACT

A process for treating aqueous effluents that contain ethyl-tert-butyl ether (ETBE) to reduce the ETBE concentration is described, characterized in that in the presence of effluents, at least one bacterium that is selected from the group that is formed by *Gordona terrae* CIP I-1889 and *Rhodococcus equi* CIP I-2053 and in the presence of at least one bacterium that is selected from the group that is formed by *Pseudomonas cepacia* CIP 1-2052, *Arthrobacter globiformis* ATCC 53596, *Bacillus coagulans* ATCC 53595, *Pseudomonas stutzerii* ATCC 53602 and *Mycobacterium vaccae* JOB5 are grown to degrade essentially all of the ETBE. The concentration of ETBE in the effluent is equal to at most 1500 mg/L. Application for the water treatment industry.

16 Claims, 1 Drawing Sheet

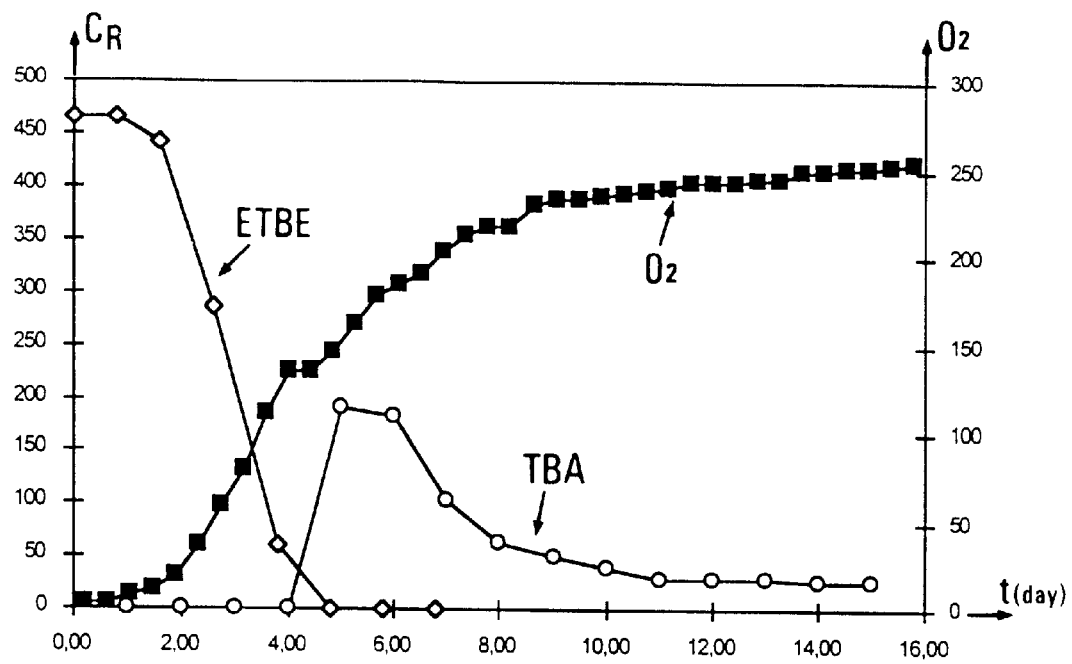

PROCESS FOR BACTERIAL TREATMENT OF EFFLUENTS THAT CONTAIN ETHYL-TERT-BUTYL ETHER

The invention relates to a process for treating effluents that use microorganisms that are able to degrade ethyl-tert-butyl ether.

It pertains particularly to the water treatment industry.

The prior art is illustrated by the following documents:

1. COWAN, R. M.: "Biodegradation of the Gasoline Oxygenates Mtbe, Etbe, Tame, TBA and Taa by Aerobic Mixed Cultures."
Hazard. Ind. Wastes, Vol. 28, 1996, pages 523–530.

2. YEH, C. K. et al.: "Anaerobic Biodegradation of Gasoline Oxygenates in Soils"
Water Environment Research, Vol. 66, No. 5, July 1, 1994, pages 744–752.

3. MORMILE, M. R. et al.: "Anaerobic Biodegradation of Gasoline Oxygenates: Extrapolation of Information to Multiple Sites and Redox Conditions"
Environmental Science and Technology, Vol. 28, No. 9, September 1, 1994.

Furthermore, Patent Application WO 98 01241 describes a process for degradation of ethers that use stocks such as *Mycobacterium vaccae* JOB5, ATCC 29678, which use propane or isopropanol for their growth phase as the sole source of carbon and energy.

It is known that the ethyl-tert-butyl ether, which is referred to below by the term ETBE, is one of the ethers that can be used as an oxygenated additive in unleaded gasolines to enhance their octane ratings. The rising use of additives such as ETBE involves large stored and transported volumes that are mixed with gasolines in particular. It is therefore necessary to know what happens to this compound in case of accidental dumping, leading to pollution of the soil and groundwater or surface waters. ETBE is an ether that is produced by condensation of ethanol on isobutene. Its structure, which comprises an ether bond as well as a tert-carbon bond, is such as to make it resistant to biodegradation by the microorganisms that are present in the environment.

Recent literature that relates to the biodegradation of alkyl ethers that are used in the gasolines indicates that the metabolism of these compounds in the environment is not a common phenomenon and that it is relatively slow, both under aerobic conditions and under anaerobic conditions (Salanitro, J. P., 1995, "Understanding the Limitations of Microbial Metabolism of Ethers Used as Fuel Octane Enhancers": Curr. Op. Biotechnol., 6:337–340).

Bacteria that have a capacity to degrade ETBE have never been isolated.

It is evident from these considerations that it is necessary to find and identify microorganisms that are able to biodegrade ETBE and to study their use in water treatment processes that make it possible to lower significantly the residual ETBE concentrations of urban or industrial residual waters or contaminated aquiferous layers, referred to under the general name of effluents, that are contaminated with this product.

New bacteria that make it possible to degrade ETBE in solution in water have been discovered.

One of the objects of the invention is to describe a process that uses these new bacteria to degrade the ETBE that is contained in solution in water, to ensure that it is used for the treatment of polluted waters.

In a more detailed manner, the invention relates to new bacterial stocks, isolated from the environment, which are able to degrade ETBE either separately or jointly. These new bacteria, which are filed at the Institut Pasteur [Pasteur Institute] (CNCM of the Institut Pasteur, 25, rue du Docteur Roux, F-75724 PARIS CEDEX 15), are *Gordona terne* CIP I-1889 (deposited under the terms of the Budapest Treaty at the CNCM on Jun. 25, 1997 as IFP-2001) and *Rhodococcus equi* CIP I-2053 (deposited under the terms of the Budapest Treaty at the CNCM on Jul. 20, 1998 as IFP-2005).

More specifically, the invention relates to a process for treating aqueous effluents that contain ethyl-tert-butyl ether (ETBE) to reduce the ETBE concentration, characterized in that at least one bacterium that is selected from the group that is formed by *Gordona terrae* CIP I-1889 and *Rhodococcus equi* CIP I-2053 is grown in the presence of said effluents, and the ETBE that is contained in the effluents is degraded by the biomass of said bacteria that are thus produced.

Implementation is easy since the pollutant is also used as a growth substrate.

According to a characteristic of the process, it is possible to grow said bacteria in the presence of said effluents and at least one compound that is selected from the group that is formed by a monosaccharide, a disaccharide, dibutyl ether, ethyl butyl ether, glycerol, tryptone, and diethylene glycol.

As a monosaccharide, it is advantageous to select glucose and/or fructose, and as a disaccharide, it is possible to select saccharose and/or lactose.

The process that results from implementing these two new bacteria separately or jointly can be applied to treat effluents that are polluted with ETBE to ensure that the ETBE concentration in the releases complies with the standards in force.

It is possible to carry out the process in batch mode or preferably continuously.

The details of the natures of the species are described in Example 3; each of the two bacteria is in accordance with the characteristics of its species.

These new bacteria were isolated from activated sludges that are collected at a sewage purification plant of urban waste waters that were treated according to specific microorganism enrichment techniques.

The resulting bacterial stocks are isolated after specific enrichment on ETBE and are tested in pure culture for their capacity to degrade ETBE.

In these experiments, it should be noted that ETBE can be provided as a single carbon source during the growth phase, but other carbon sources can be added at a concentration of between 10 and 50 g/l of medium, such as glucose, saccharose, glycerol or tryptone during the cultivation of one or two new bacteria. ETBE concentrations of up to 1500 mg/L, for example 10 to 1000 mg/L and preferably from 50 to 400 mg/L, are degraded by the new bacteria at rates that can go up to 100% for ETBE contents that are particularly between 50 and 400 mg/L. This suggests that the use of a reactor to remove pollution from the effluents that contain ETBE can optionally comprise a dilution stage to achieve the concentration that is accepted by the new bacteria. Under these concentration conditions, the new bacteria are able to degrade ETBE to a significant extent, i.e., 20% to 100% over periods of less than 200 hours and generally between 50 and 150 hours.

According to a preferred characteristic, it is possible to degrade the ethyl-tert-butyl ether that is contained in the effluents by the biomass of said stocks in the presence of at least one other stock that is selected from the group that is formed by *Pseucomonas cepacia* CIP I-2052 (deposited under the terms of the Budapest Treaty at the CNCM, Institut Pasteur, Paris, France on Jul. 20, 1998 as IFP 2004), *Arthrobacter globiformis* ATCC 53596, *Bacillus coagulans* ATCC 53595, *Pseudomonas stutzerii* ATCC 53602, and *Mycobacterium vaccae* JOB5 to mineralize essentially all of the ETBE and more particularly tert-butyl alcohol (TBA), an intermediate degradation compound that is formed.

The bacteria above are described in U.S. Pat. No. 4,855,051 and WO 9801241. They can be introduced preferably at the same time as *Gordona terrae* or *Rhodococcus equi* into the medium that comprises the ETBE that is contained in the aqueous effluents, and their growth phase will start when tert-butyl alcohol is formed. They can also be introduced later, however, when the ETBE has degraded into TBA.

The use of these bacteria for treating effluents that are polluted with ETBE can be carried out in the following way: for example in a biofilter where the bacteria are attached to a mineral or organic substrate, or they can be added as an inoculum to sewage purification plant sludges.

The flow rate of effluents that contain ETBE that are treated in the biofilter can be between 0.03 and 7 L/L of biofilter per hour, advantageously 0.1 and 4 L/L of biofilter per hour, and preferably 0.3 to 2 L/L of biofilter per hour.

BRIEF DESCRIPTION OF THE DRAWING

The FIGURE shows the residual concentration (CR) of ETBE and TBA and the oxygen that is consumed based on time t which is expressed in days

EXAMPLE 1

The method of isolating bacteria that is used constitutes an important point for obtaining new bacteria.

Samples of activated sludges were taken at the Achéres waste water treatment plant (Yvelines, 78) and inoculated in a flask at a dry-material concentration on the order of 300 mg/L in a respirometric reactor (Sapromat, Voith, Germany) that makes it possible to measure continuously the oxygen demand of the culture in the following saline medium:

$KH_2PO_4$ . . . 85 mg $K_2HPO_4$ . . . 217.5 mg $Na_2HPO_4, 2H_2O$ . . . 334 mg $NH_4Cl$ . . . 5 mg $MgSO_4, 7H_2O$ . . . 22.5 mg $CaCl_2, 2H_2O$ . . . 36.4 mg $FeCl_3, 6H_2O$ . . . 0.25 mg $H_2O$ . . . q.s.p. 1 liter and in which ETBE is added at the final concentration of 100 mg/L. In parallel, a flask that does not contain ETBE is also incubated to measure the oxygen demand of the microflora that is introduced which corresponds to the respiration that is linked to the degradation of organic materials in suspension in the activated sludges. By comparing the oxygen demand curves of the two types of flasks, it is possible to estimate the consumption of ETBE. The calculation of the theoretical oxygen demand (D.Th.O) is done based on the added ETBE quantity and makes it possible to determine when consumption is total, knowing that the theoretical oxygen demand for 1 mg of ETBE is 2.82 mg of oxygen. A new ETBE aliquot is then added, and its consumption is tracked. This operation is repeated three times in all. At the end of these operations, the selected microflora is sampled, and the stocks that are present are isolated in a conventional way by spreading them on a complete solid medium whose composition is as follows:

Bacto-tryptone . . . 10 g yeast extract . . . 5 g

NaCl . . . 5 g glucose . . . 1 g bacto-agar . . . 20 g $H_2O$ . . . q.s.p. 1 liter The various bacterial stocks are purified and are tested for their capacity to degrade ETBE. Two new bacteria, CIP I-1889 and CIP I-2053, that are thus isolated have proven able to degrade ETBE and were thus identified.

EXAMPLE 2

The following medium is used to cultivate bacteria:

$KH_2PO_4$ . . . 85 mg $K_2HPO_4$ . . . 217.5 mg $Na_2HPO_4, 2H_2O$ . . . 334 mg $NH_4Cl$ . . . 5 mg $MgSO_4, 7H_2O$ . . . 22.5 mg $CaCl_2, 2H_2O$ . . . 36.4 mg $FeCl_3, 6H_2O$ . . . 0.25 mg $H_2O$ . . . q.s.p. 1 liter pH=6.8

Each bacterium is inoculated in a flask of this medium in which ETBE at the final concentration of 100 mg/L is added.

The cultures are incubated at 30° C.

The residual ETBE concentrations are determined in the following way:

A culture sample is taken and injected into a piece of gas chromatography equipment (CPG) that is equipped with an integrator which calculates the residual concentrations by integrating the surface areas of various peaks that are obtained on the chromatograms. The results that are obtained are illustrated in Table 1.

TABLE 1

ETBE Degradation Capacity of the New Bacteria

| Experiment No. | Tested Bacteria | % of ETBE that is Degraded | Duration |
| --- | --- | --- | --- |
| 1 | Bacterium CIP I-1889 | 100% | 50 hours |
| 2 | Bacterium CIP I-2053 | 100% | 150 hours |

EXAMPLE 3

The isolated bacteria that degrade ETBE were subjected to morphological examination using the optical microscope, with Gram staining, to various biochemical tests and were identified according to the classification methods of "Bergey's Manual for Determinative Bacteriology."

The results of all of the biochemical tests are summarized in Table 2.

TABLE 2

Identifying Qualities of the New Bacteria

| Conventional Qualities Studied | Bacterium CIP I-1889 | Bacterium CIP I-2053 |
|---|---|---|
| Catalase | positive | positive |
| Oxydase | negative | — |
| Reductase nitrate | positive | positive |
| Reductase nitrite | negative | negative |
| Urea | positive | positive |
| ONPG hydrolysis | negative | — |
| Simmons citrate | negative | negative |
| Esculin | negative | positive |
| Pyrazinamidase | positive | slightly positive |
| Amylase | positive | negative |
| Proteolysis | negative | negative |
| DNase | negative | slightly positive |
| Tween 80 esterase | positive | negative |
| Pyrrolidonyl arylamydase | — | positive |
| Alkaline phosphatase | — | slightly positive |
| Voges-Proskauer reaction | negative | — |

To complete the identification of bacterium CIP I-1889, an analysis of its growth on various sugars was produced (Table 3).

TABLE 3

Growth on Sugar of Bacterium CIP I-1889

| Tested Sugar | Growth of the bacterium CIP I-1889 |
|---|---|
| D-glucose | positive |
| Saccharose | positive |
| Glycerol | positive |
| D-fructose | positive |
| D-mannose | positive |
| Mannitol | slightly positive |
| Sorbitol | slightly positive |
| Maltose | slightly positive |
| Trehalose | slightly positive |
| Xylitol | positive |
| Raffinose | positive |
| D-turanose | positive |
| D-lyxose | slightly positive |
| D-fucose | slightly positive |
| L-fucose | positive |
| D-arabitol | positive |
| L-arabitol | slightly positive |
| Inositol | negative |
| Rhamnose | negative |
| Cellobiose | negative |
| Galactose | negative |

Bacterium CIP I-1889, which is a strict gram-positive aerobic bacillus that is coryneform, immobile, and non-branching and that forms on an ordinary nutrient-medium box colonies that are dyed with a bright orange pigment, was identified as a *Gordona terrae* stock.

Bacterium CIP I-2053, which is a strict gram-positive aerobic bacillus that is coryneform, immobile, branching and that forms on an ordinary nutrient-medium box colonies that are dyed with a light pink pigment, was identified as a *Rhodococcus equi* stock.

EXAMPLE 4

The *Gordona terrae* CIP I-1889 stock is cultivated on 2 L of the following complete medium:

Bacto-tryptone . . . 10 g yeast extract . . . 5 g

NaCl . . . 5 g glucose . . . 1 g $H_2O$ . . . q.s.p. 1 liter while being stirred at 30° C., for 48 hours. The cells are collected by centrifuging and are then introduced into a 3 L percolating biofilter system. The biofilter contains 3 L of a fixed bed that consists of a porous material which can be of a varied mineral or organic nature and which, in this example, consists of pumice stone. This material constitutes the substrate to which the bacteria are attached and develop upon contact of ETBE as a growth substrate.

When the inoculation of the substrate is done, it contains an immobilized biomass of about 1 g/L. The biofilter, which is kept at a temperature of 20° C., is then fed through the top with a synthetic aqueous effluent that percolates through the bed of immobilized bacteria and that contains the following salts:

$KH_2PO_4$ . . . 85 mg $K_2HPO_4$ . . . 217.5 mg $Na_2HPO_4, 2H_2O$ . . . 334 mg $NH_4Cl$ . . . 5 mg $MgSO_4, 7H_2O$ . . . 22.5 mg $CaCl_2, 2H_2O$ . . . 36.4 mg $FeCl_3, 6H_2O$ . . . 0.25 mg $H_2O$ . . . q.s.p. 1 liter as well as ETBE at a concentration that is between 100 and 200 mg/L. The injection flow rate is between 0.3 and 0.6 L/L of biofilter per hour. A pump for recirculating the liquid that is removed from the bottom of the biofilter and recycled upward makes it possible to vary the percolation flow rate independently of the effluent: supply. Aeration is ensured by the circulation of air rising through the substrate. In this example, the aeration flow rate is between 0.5 and 2 L/L of biofilter per hour.

A vent makes it possible to evacuate the gases of the biofilter, and the treated effluent is drawn off at the bottom of the biofilter.

The ETBE is metered by gas chromatography at the input and output of the biofilter, and this makes it possible to calculate the percentage of degraded ETBE, which is typically 100%.

EXAMPLE 5

ISOLATION AND IDENTIFICATION OF A BACTERIUM THAT DEGRADES TERT-BUTANOL (TBA)

It was shown in Example 2 that the new bacteria CIP I-1889 and CIP I-2053 are able to degrade all of the ETBE that is provided to them. Even so, metering by gas chromatography that is done at the end of the ETBE degradation test shows the appearance of a new product, which was identified as being tert-butanol or TBA, an intermediate product in the biodegradation path of ETBE. This peak, however, did not appear when activated sludges were used directly as in Example 1. In the activated sludges, there is therefore another bacterium that is able to degrade the TBA that is produced by the two new bacteria when they are cultivated on ETBE. This new bacterium was isolated since its presence in the activated sludges makes it possible to achieve essentially complete biodegradation of ETBE without accumulating its intermediate degradation product, TBA.

A sample of activated sludges that makes it possible to select the two new bacteria that degrade ETBE is then inoculated into a flask of the saline medium which is described in Example 1 at a ratio of 10% and to which TBA is added at the final concentration of 100 mg/L. The consumption of TBA is measured by metering of residual TBA by gas chromatography. When all the added TBA has been consumed, a sampling of the microflora thus selected is carried out, and the bacteria that are present are isolated in a conventional way by spreading in a complete solid medium whose composition is as follows:

| | |
|---|---|
| Bacto-tryptone | 10 g |
| yeast extract | 5 g |
| NaCl | 5 g |
| glucose | 1 g |
| bacto-agar | 20 g |
| $H_2O$ | q.s.p. 1 liter |

The various bacterial stocks are purified and are tested for their capacity to degrade TBA. A new bacterium, CIP I-2052, that is thus isolated has proven capable of degrading TBA after having been cultivated in the following saline medium:

| | |
|---|---|
| $KH_2PO_4$ | 1.4 g |
| $KH_2HPO_4$ | 1.7 g |
| $NaNO_3$ | 1.5 g |
| $MgSO_4, 7H_2O$ | 0.5 g |
| $CaCl_2, 2H_2O$ | 0.04 g |
| $FeCl_3, 6H_2O$ | 0.012 g |
| vitamin solution | 1 mL |
| $H_2O$ | q.s.p. 1 liter |

TBA at a final concentration on the order of 100 mg/L is added to this medium. The result that is obtained is presented in Table No. 4.

TABLE 4

Capacity for Degrading TBA of the New Bacterium CIP I-2052

| Experiment No. | Bacteria Tested | % of degraded TBA | Duration |
|---|---|---|---|
| 1 | Bacterium CIP I-2052 | 100% | 96 hours |

Isolated bacterium CIP I-2052 that degrades TBA was subjected to morphologic examination using the optical microscope, with Gram staining, to various biochemical tests and identified according to the classification methods of "Bergey's Manual for Determinative Bacteriology." It is a strict gram-negative aerobic bacillus that is mobile by ciliature of the polar type, non-sporulated, non-capsulated, unbranched and that forms non-pigmented colonies on an ordinary nutrient-medium box.

The results of all the biochemical tests are summarized in Table 5. To complete the identification of bacterium CIP I-2052, an analysis was carried out on gallery API 20 NE, and the positive qualities are presented in Table No. 6.

Bacterium CIP I-2052 was identified as being a *Pseudomonas cepacia* stock.

TABLE 5

Identification Qualities of New Bacterium CIP I-2052

| Conventional Qualities Studied | Bacterium CIP I-2052 |
|---|---|
| Catalase | positive |
| Oxydase | positive |
| Reductase nitrate | negative |
| Reductase nitrite | negative |
| Urea | positive |
| Hydrolysis of ONPG | negative |
| Simmons citrate | negative |
| Esculin | positive |
| Amylase | negative |
| Proteolysis | slightly positive |
| DNase | negative |
| Tween 80 esterase | positive |
| Malonate | negative |
| Indole | negative |

TABLE 6

Positive Qualities That Are Obtained on Gallery API 20 NE of Bacterium CIP I-2052

| Tested Quality | Response to Gallery API 20 NE |
|---|---|
| Urea | positive |
| Esculin | positive |
| Gelatin | positive |
| Glucose (assimilation) | positive |
| D-mannose | positive |
| Mannitol | positive |
| N-acetyl-glucosamine | positive |
| Maltose | positive |
| Gluconate | positive |
| Adipate | positive |
| Malate | positive |
| Phenyl-acetate | positive |
| Citrate | slightly positive |
| Oxydase | positive |

EXAMPLE 6

TOTAL BIODEGRADATION OF ETBE BY A RECONSTITUTED MIXED CULTURE THAT COMPRISES *G. TERRAE* CIP I-1889 AND *P. CEPACIA* CIP I-2052

Since the bacteria *G. terrae* CIP I-1889 and *R. equi* CIP I-2053 are capable of degrading ETBE into TBA and bacterium *P. cepacia* CIP I-2052 is capable of using TBA as a carbon source, it is advantageous to have these two groups of new bacteria act jointly to achieve essentially total mineralization of the ETBE that is contained in the aqueous effluents.

A preculture of *G. terrae* CIP I-1889 and a preculture of *P. cepacia* CIP i-2052 were produced. These precultures are used to produce together a mixed culture in a respirometric reactor (Sapromat, Voith, Germany) that makes it possible to measure continuously the oxygen demand of the culture in the following saline medium:

| | |
|---|---|
| $KH_2PO_4$ | 1.4 g |
| $K_2HPO_4$ | 1.7 g |
| $NaNO_3$ | 1.5 g |
| $MgSO_4, 7H_2O$ | 0.5 g |
| $CaCl_2, 2H_2O$ | 0.04 g |

| -continued | |
|---|---|
| FeCl$_3$, 6H$_2$O | 0.012 g |
| vitamin solution | 1 ml |
| H$_2$O | q.s.p. 1 liter | and in which ETBE is added at the final concentration of 460 mg/L. The experiment was carried out at 30° C. The saline culture medium (225 mL) is inoculated with precultures to obtain a ratio that is on the order of 2 (in dry weight) between the stock of P. cepacia CIP I-2052 and the stock of G. terrae CIP I-1889. In particular, a flask that is inoculated in the same way with the two microorganisms but that does not contain ETBE is also incubated to measure the oxygen demand of the microflora that is introduced without carbon substrate, whereby this value corresponds to the endogenic respiration. By comparing the oxygen demand curves of the two types of flasks, it is possible to estimate the consumption of ETBE. Furthermore, samples are taken at the beginning of the experiment and then daily to determine by gas chromatography the residual quantities of ETBE and TBA. The results of this experiment are presented in FIG. 1, which shows that residual concentrations (CR) of ETBE and TBA and the oxygen that is consumed based on time t is expressed in days. In this FIGURE, the values of consumed oxygen are values that are measured in the presence of ETBE and derived from those that are obtained in the control without substrate. Knowing that the theoretical oxygen demand (D.Th.O.) is 2.82 mg of oxygen per 1 mg of ETBE, we were able to calculate the theoretical oxygen demand that corresponds to the quantity of ETBE that is added in the experiment. The ratio between the measured value of oxygen demand and the theoretical oxygen demand provides us with a measure of the percentage of mineralization of ETBE, which in this case is greater than 90%, typically 92.5%.

The preceding examples can be repeated with similar success by substituting the generically or specifically described reactants and/or operating conditions of this invention for those used in the preceding examples.

The entire disclosure of all applications, patents and publications, cited above, and of corresponding French application No. 97/09,455, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. Process for treating aqueous effluents that contain ethyl-tert-butyl ether (ETBE) to reduce the ETBE concentration, characterized in that at least one bacterium that is selected from the group consisting of Gordona terrae CIP I-1889 and Rhodococcus equi CIP I-2053 is grown in the presence of said effluents and the ETBE that is contained in the effluents is degraded by the biomass of said bacteria that are thus produced.

2. A process according to claim 1, wherein said bacterium is preselected in an activated sludge before being inoculated in the presence of said effluent that contains ETBE.

3. A process according to claim 1, wherein the ETBE concentration of the effluent is at most equal to 1500 mg/L.

4. A process according to claim 1, wherein the ETBE concentration of the effluent is between 50 and 400 mg/L.

5. A process according to claim 1, wherein said bacteria is developed on a biofilter system with a suitable the effluent that contains ETBE is introduced into the biofilter at a flow rate of 0.03 to 7 L/L of biofilter and per hour, and the effluent from which at least part of the ETBE is removed is drawn off.

6. A process according to claim 1, wherein ETBE is degraded by the biomass of said bacteria in the presence of at least one other stock selected from the group consisting of Pseudomonas cepacia CIP 1-2052, Arthrobacter globiformis ATCC 53596, Bacillus coagulans ATCC 53595, Pseudonas stutzerii ATCC 53602 and Mycobacterium veccae JOB5 for degrading essentially all the ETBE.

7. A process according to claim 1, wherein said bacterium is grown in the presence of said effluents, and at least one compound is selected from the group consisting of a monosaccharide, a disaccharide, dibutyl ether, ethylbutyl ether, glycerol, tryptone, and diethylene glycol.

8. A process according to claim 7, wherein the monosaccharide is glucose or fructose, and the disaccharide is saccharose or lactose, and one of the monosaccharides and disaccharides is employed.

9. A process for treating aqueous effluents that contain ethyl-tert-butyl ether (ETBE) to reduce the ETBE concentration, comprising growing the bacterium Gordona terrae (CIP 1-1889) in the presence of said effluents, whereby the ETBE contained in the (effluents is degraded by the resultant biomass of said bacteria.

10. A process according to claim 9, wherein said bacterium is preselected in an activated sludge before being inoculated in the presence of said effluent that contains ETBE.

11. A process according to claim 9, wherein the ETBE concentration of the effluent is at most equal to 1500 mg/L.

12. A process according to claim 9, wherein the ETBE concentration of the effluent is between 50 and 400 mg/L.

13. A process according to claim 9, wherein said bacteria is developed on a biofilter, the effluent that contains ETBE is introduced into the biofilter at a flow rate of 0.03 to 7 L/L of biofilter and per hour, and the effluent from which at least part of the ETBE is removed is drawn off.

14. A process according to claim 9, wherein ETBE is degraded by the biomass of said bacteria in the presence of at least one other stock selected from the group consisting of Pseudomonas cepacia CIP I-2052, Arthrobacter globiformis ATCC 53596, Bacillus coagulans ATCC 53595, Pseudomonas stutzerii ATCC 53602 and Mycobacterium vaccae JOB5 for degrading essentially all the ETBE.

15. A process according to claim 9, wherein said bacterium is grown in the presence of said effluents, and at least one compound is selected from the group consisting of a monosaccharide, a disaccharide, dibutyl ether, ethylbutyl ether, glycerol, tryptone, and diethylene glycol.

16. A process according to claim 14, wherein the monosaccharide is glucose or fructose, and the disaccharide is saccharose or lactose, and at least one of the monosaccharides and disaccharides is employed.

* * * * *